United States Patent
O'Connor (10) Patent No.: US 12,322,095 B2
(45) Date of Patent: Jun. 3, 2025

(54) ADJUSTING APPEARANCE OF OBJECTS IN MEDICAL IMAGES

(71) Applicant: Nuvasive, Inc., San Diego, CA (US)

(72) Inventor: Sean O'Connor, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 466 days.

(21) Appl. No.: 17/760,987

(22) PCT Filed: Sep. 24, 2020

(86) PCT No.: PCT/US2020/052537
§ 371 (c)(1),
(2) Date: Mar. 16, 2022

(87) PCT Pub. No.: WO2021/062024
PCT Pub. Date: Apr. 1, 2021

(65) Prior Publication Data
US 2022/0375078 A1 Nov. 24, 2022

Related U.S. Application Data

(60) Provisional application No. 62/905,306, filed on Sep. 24, 2019.

(51) Int. Cl.
| | |
|---|---|
| *G06T 7/00* | (2017.01) |
| *G06T 5/50* | (2006.01) |
| *G06T 5/70* | (2024.01) |
| *G06T 5/94* | (2024.01) |

(52) U.S. Cl.
CPC .............. *G06T 7/0012* (2013.01); *G06T 5/50* (2013.01); *G06T 5/70* (2024.01); *G06T 5/94* (2024.01); *G06T 2207/20192* (2013.01); *G06T 2207/20221* (2013.01); *G06T 2207/20224* (2013.01); *G06T 2207/30004* (2013.01); *G06T 2207/30168* (2013.01)

(58) Field of Classification Search
None
See application file for complete search history.

(56) References Cited

U.S. PATENT DOCUMENTS

| | | |
|---|---|---|
| 8,526,700 B2 | 9/2013 | Isaacs |
| 2016/0117823 A1* | 4/2016 | Isaacs ..................... G06T 11/60 715/863 |
| 2017/0165008 A1 | 6/2017 | Finley |
| 2017/0325897 A1 | 11/2017 | Isaacs et al. |

OTHER PUBLICATIONS

PCT International Search Report for PCT Application No. PCT/US2020/052537 mailed Jan. 25, 2021 (3 pages).
PCT Written Opinion for PCT Application No. PCT/US2020/052537 mailed Jan. 25, 2021 (9 pages).

* cited by examiner

Primary Examiner — Leon Flores

(57) ABSTRACT

Disclosed herein are systems and methods for adjusting appearance of objects in medical images.

12 Claims, 8 Drawing Sheets

Baseline (left) and Overlay (right) that view the same anatomy. Overlay contains a metal instrument.

Alignment of anatomy determines how the two images overlap

Ideal metal boost: overlap area is a composite of overlay (just in metal) and baseline (everywhere else)

ADJUSTING APPEARANCE OF OBJECTS IN MEDICAL IMAGES

CROSS REFERENCE

This application is a National Stage Application of PCT/US2020/052537, filed Sep. 24, 2020, which is a non-provisional of, and claims the benefit of, U.S. Provisional patent application Ser. No. 62/905,306 filed Sep. 24, 2019, the entire contents of which are hereby expressly incorporated by reference into this disclosure as if set forth in their entirety herein.

BACKGROUND

Medical imaging modalities such as computed tomography (CT), X-ray, or fluoroscopic generate a fair amount of ionizing radiation which has been identified as a potential cause for a host of medical problems.

SUMMARY

Image enhancement platform are developed to take low-quality, low-dose images and improve them to look like conventional full-dose images. Image enhancement platforms, e.g., LessRay may offer the physician and hospital system the opportunity to use significantly reduced radiation imaging in the operation room. The image enhancement platform's fundamental scheme may rely on a "baseline" image (e.g., a high quality and full dose image) aligned with an overlapping lower-quality low dose "overlay" image. The overlay image may contain different information than the baseline image. As an example, the overlay image may contain surgical tools that only appear in the overlay image. The aligned composite image of the baseline and overlay image can provide high image quality to the information details that are only in the low-quality "overlay" image. However, image enhancement platforms such as LessRay may face various technical challenges due to its dependence on low quality, and low-dose of images. Metal objects such as surgical tools can become too faint in the standard flat blend of the two images, e.g., in the usual alternating blend, metal appears (intentionally) partially transparent.

Disclosed herein are systems and methods for adjusting appearance of objects of interest in the composite image. The systems and methods herein may use a spatially-varying blending scheme that combines the higher-quality appearance of anatomy in the baseline image with the dark, opaque appearance of objects of interest from the overlay image. In the overlap region, pixels from each image can be adaptively blended according to how likely they are metal.

The systems and methods herein use a "difference" image technique in order to exploit alignment of the baseline image and the overlay image to locate objects to be enhanced. When correctly aligned and contrast-equalized, the alignment can be to used cancel out common anatomy and isolate unique items in each image. Items that are darker in color (e.g., lower intensity) in the aligned image can be selectively enhanced, under the assumption that they can be objects of interest, e.g., metal surgical instrument. Disclosed herein, in some embodiments, are methods for adjusting appearance of objects in medical images, the method comprising: receiving, by a computer, a baseline image of a subject containing one or more objects therewithin, the baseline image taken with a baseline image quality and a baseline radiation dosage; receiving, by the computer, an overlay image of the subject containing the one or more objects therewithin, the overlay image taken with an overlay image quality and an overlay radiation dosage; transforming, the baseline image using a spatial transformation thereby generating a transformed baseline image, wherein the transformation comprises one or more of spatial scaling, translation, and rotation factors; equalizing image intensity, image contrast, or both of the baseline image and the overlay image by estimating an image equalizing transformation between the baseline image and the overlay image; rescaling, by the computer, the overlay image using the scaling factor and the offset thereby generating a rescaled overlay image; generating, by the computer, a difference image of the transformed baseline image and the rescaled overlay image; generating, by the computer, a smoothed weight mask, wherein each pixel of the smoothed weight mask is a weighting; and generating, by the computer, a composite image of the baseline image and the overlay image with contribution of the baseline image and the overlay image determined by the smoothed weight mask. In some embodiments, the overlay image quality is lower than the baseline image quality. In some embodiments, a first signal to noise ration of the overlay image is lower than a second signal to noise ratio of the baseline image. In some embodiments, the image equalizing transformation is a linear transformation determined by a scaling factor and an offset. In some embodiments, the difference image is obtained by subtracting the rescaled overlay image from the transformed baseline image. In some embodiments, the weighting is determined by intensity of a corresponding pixel in the difference image, estimated intensity of background pixels in the difference image, and estimated intensity of one or more objects in the difference image, or a combination thereof.

Disclosed herein, in some embodiments, are methods for adjusting appearance of objects in medical images, the method comprising: receiving, by a computer, a baseline image of a subject containing one or more objects therewithin, the baseline image taken with a baseline image quality and a baseline radiation dosage; receiving, by the computer, an overlay image of the subject containing the one or more objects therewithin, the overlay image taken with an overlay image quality and an overlay radiation dosage; transforming, the baseline image using a spatial transformation thereby generating a transformed baseline image, wherein the transformation comprises one or more of spatial scaling, translation, and rotation factors; equalizing image intensity, image contrast, or both of the baseline image and the overlay image by estimating an image equalizing transformation between the baseline image and the overlay image; rescaling, by the computer, the overlay image using the scaling factor and the offset thereby generating a rescaled overlay image; generating, by the computer, a difference image of the transformed baseline image and the rescaled overlay image; generating, by the computer, a smoothed weight mask, wherein each pixel of the smoothed weight mask is a weighting; and generating, by the computer, a composite image of the baseline image and the overlay image with contribution of the baseline image and the overlay image determined by the smoothed weight mask. In some embodiments, the overlay image quality is lower than the baseline image quality. In some embodiments, a first signal to noise ration of the overlay image is lower than a second signal to noise ratio of the baseline image. In some embodiments, the image equalizing transformation is a linear transformation determined by a scaling factor and an offset. In some embodiments, the difference image is obtained by subtracting the rescaled overlay image from the transformed baseline image. In some embodiments, the weighting is determined by intensity of a corresponding pixel in the difference image, estimated intensity of background pixels in the difference image, and estimated intensity of objects in the difference image, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Disclosed herein, in some embodiments, are methods for adjusting appearance of objects in medical images, the method comprising: receiving, by a computer, a baseline image of a subject containing one or more objects therewithin, the baseline image taken with a baseline image quality and a baseline radiation dosage; receiving, by the computer, an overlay image of the subject containing the one or more objects therewithin, the overlay image taken with an overlay image quality and an overlay radiation dosage; transforming, the baseline image using a spatial transformation thereby generating a transformed baseline image, wherein the transformation comprises one or more of spatial scaling, translation, and rotation factors; equalizing image intensity, image contrast, or both of the baseline image and the overlay image by estimating an image equalizing transformation between the baseline image and the overlay image; rescaling, by the computer, the overlay image using the scaling factor and the offset thereby generating a rescaled overlay image; generating, by the computer, a difference image of the transformed baseline image and the rescaled overlay image; generating, by the computer, a smoothed weight mask, wherein each pixel of the smoothed weight mask is a weighting; and generating, by the computer, a composite image of the baseline image and the overlay image with contribution of the baseline image and the overlay image determined by the smoothed weight mask. In some embodiments, the overlay image quality is lower than the baseline image quality. In some embodiments, a first signal to noise ration of the overlay image is lower than a second signal to noise ratio of the baseline image. In some embodiments, the image equalizing transformation is a linear transformation determined by a scaling factor and an offset. In some embodiments, the difference image is obtained by subtracting the rescaled overlay image from the transformed baseline image. In some embodiments, the weighting is determined by intensity of a corresponding pixel in the difference image, estimated intensity of background pixels in the difference image, and estimated intensity of one or more objects in the difference image, or a combination thereof.

Disclosed herein, in some embodiments, are methods for adjusting appearance of objects in medical images, the method comprising: receiving, by a computer, a baseline image of a subject containing one or more objects therewithin, the baseline image taken with a baseline image quality and a baseline radiation dosage; receiving, by the computer, an overlay image of the subject containing the one or more objects therewithin, the overlay image taken with an overlay image quality and an overlay radiation dosage; transforming, the baseline image using a spatial transformation thereby generating a transformed baseline image, wherein the transformation comprises one or more of spatial scaling, translation, and rotation factors; equalizing image intensity, image contrast, or both of the baseline image and the overlay image by estimating an image equalizing transformation between the baseline image and the overlay image; rescaling, by the computer, the overlay image using the scaling factor and the offset thereby generating a rescaled overlay image; generating, by the computer, a difference image of the transformed baseline image and the rescaled overlay image; generating, by the computer, a smoothed weight mask, wherein each pixel of the smoothed weight mask is a weighting; and generating, by the computer, a composite image of the baseline image and the overlay image with contribution of the baseline image and the overlay image determined by the smoothed weight mask. In some embodiments, the overlay image quality is lower than the baseline image quality. In some embodiments, a first signal to noise ration of the overlay image is lower than a second signal to noise ratio of the baseline image. In some embodiments, the image equalizing transformation is a linear transformation determined by a scaling factor and an offset. In some embodiments, the difference image is obtained by subtracting the rescaled overlay image from the transformed baseline image. In some embodiments, the weighting is determined by intensity of a corresponding pixel in the difference image, estimated intensity of background pixels in the difference image, and estimated intensity of objects in the difference image, or a combination thereof.

Certain Terms

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As disclosed herein, the objects of interest, instruments, and/or surgical tools to be enhanced using the methods, systems, and media herein are not limited to metal. Such objects, instruments, and/or surgical tools may contain any material that may be opaque or dense in a sense that they can obstruct anatomical information. In some embodiments, when the imaging modality is radiography or X-ray related, the objects, instruments and/or surgical tools can be radiodense. With other imaging modalities, the objects, instruments, and/or surgical tools may not contain any metal but may contain one or more types of other materials that obstruct the anatomical information.

In some embodiments, the metal objects herein are equivalent to opaque objects or dense objects with the specific imaging modality used. For example, the metal objects disclosed herein may comprise glass or plastic is opaque when the imaging modality is Ultrasound.

In some embodiments, the baseline and overlay images disclosed herein can be acquired using one or more different imaging modalities, such as X-ray, CT, MRI, ultrasound, SPECT, PET, etc.

Overview

The systems and methods herein hinge on finding the difference of the baseline image and the overlay image, i.e., difference image, and looking for large discrepancies, e.g., difference in gray level. If both images have the same content, and alignment is perfect, the difference of the two images can be essentially a featureless flat image containing only background noise. Any objects found only in one image can then stand out fairly dramatically in the difference image. Depending on how the difference image is calculated, same objects may appear differently in the difference image. For example, dark pixels, e.g., metal, only in the overlay image may manifest as a bright area in the difference image if it is calculated as baseline minus overlay image. The brightness or image intensity in the difference image can be used to create the spatially-varying mask for blending, e.g., the brighter the pixel, the more it gets blended in the overlay image.

Based on how the difference image is calculated, e.g., overlay minus baseline, the methods can intentionally look for lighter areas in the difference image. If the difference is calculated as baseline minus overlay, the methods may look for darker areas in the difference image. Dark objects that are unique to the baseline may appear darker than the background in the difference image. These darker pixels may be assigned a low (or zero) proportion of overlay image to blend from. The result is that the composite may contain dark objects, e.g., metal, from both images. If there happen to be some lighter area in the overlay image (for example a washed-out bright saturated region), that region may be built from the baseline in the composite image.

In some embodiments, the systems and methods herein advantageously sidestep the difficult task of explicit segmentation of objects, e.g., finding precise boundaries of metal edges, so metal areas can be cut-and-pasted on top of the baseline, where small errors in segmentation can lead to visually obvious artifacts. In the intermediate region between metal and nonmetal, the blend using the systems methods herein advantageously smoothly transitions between the two images to avoid creating any visible border. Further, the two images are advantageously matched in contrast and brightness before blending, so occasional misclassified pixels tend to not stand out. In regions of anatomy, both images may have similar grayscale values so a misidentification may not result in much change in pixel value, while inside metal an occasional misclassified pixel tends to be visually tolerable. Avoiding segmentation also makes the systems and methods fast in adjusting appearance of objects of interest so that they can be unambiguously visible to greatly facilitate decision making and/or surgical movement by the surgeon.

Figure 1:
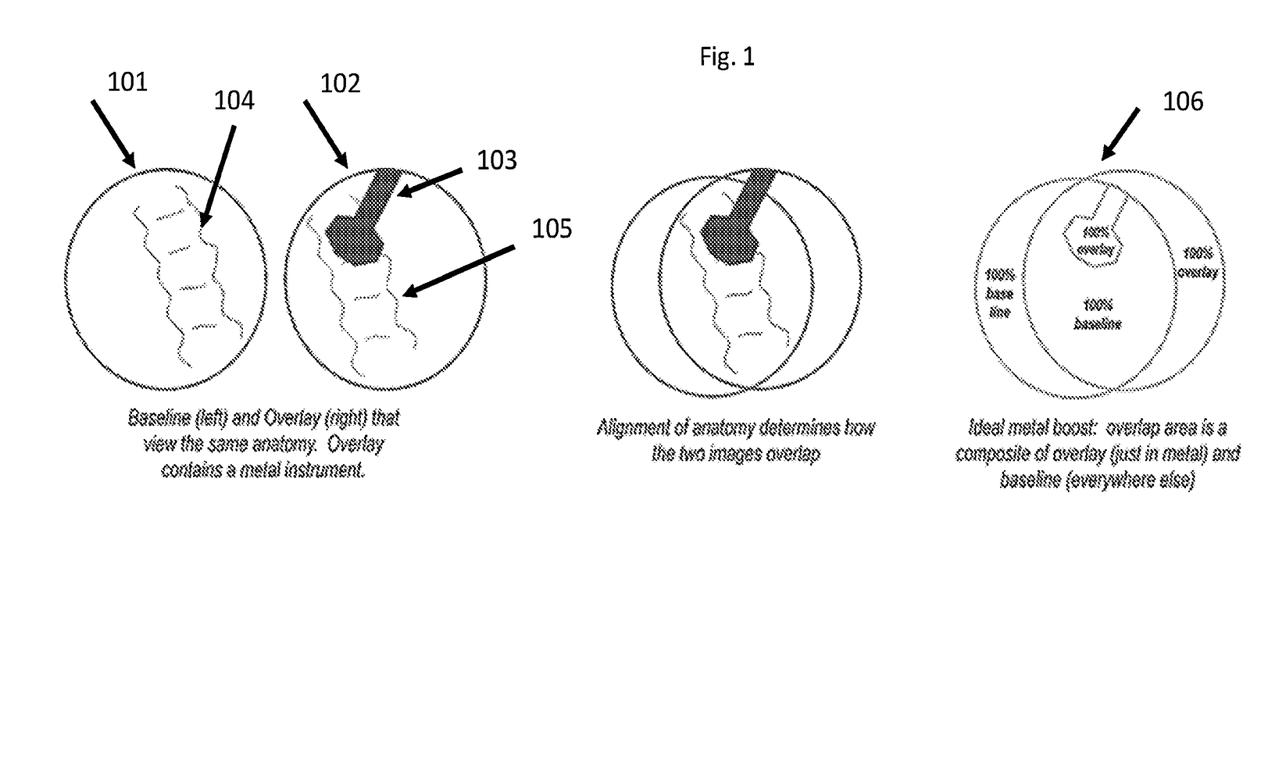
FIG. 1 shows an exemplary embodiment of the systems and methods that uses the difference image for adjusting appearance of objects of interest, e.g., metal objects; in this case, an image containing just the metal from the overlay image is placed on top of anatomy from baseline image.

FIG. 1 shows an exemplary embodiment of enhancing the appearance of objects 103. In this case, the overlap area 104 is a composite of metal 103 from the overlay image 102 and anatomy 105 from the baseline image 101. In some embodiments, the blending may smoothly transition between 100% baseline image and 100% overlay image to avoid visual artifacts at the transition at object's edge(s).

Spatial Transformation

Figure 2A:
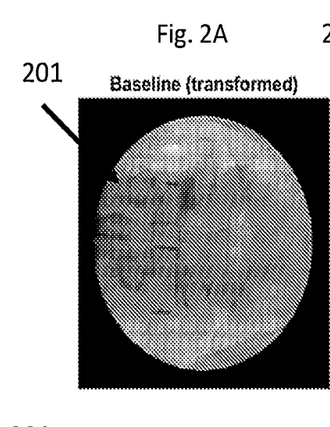
FIGS. 2A-2F show exemplary baseline images after spatial transformation to align with the overlay images (FIGS. 2A, 2D), overlay images rescaled with an image equalizing transformation (FIGS. 2B, 2E), and difference images obtained by subtracting the rescaled overlay image from the transformed baseline image (FIGS. 2C, 2F)
Figures 2B, 2C:
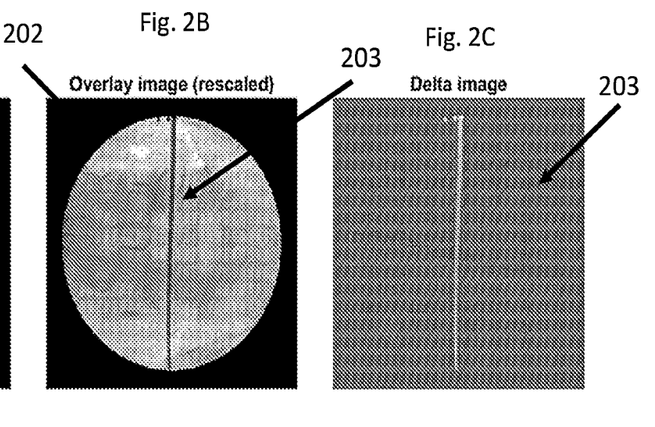
Figure 2D:
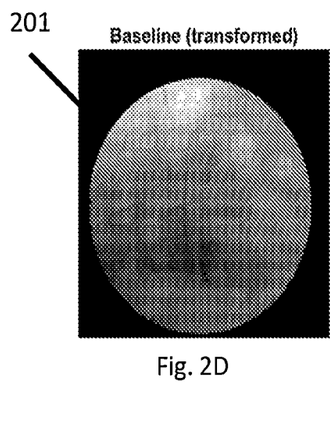
Figure 4:
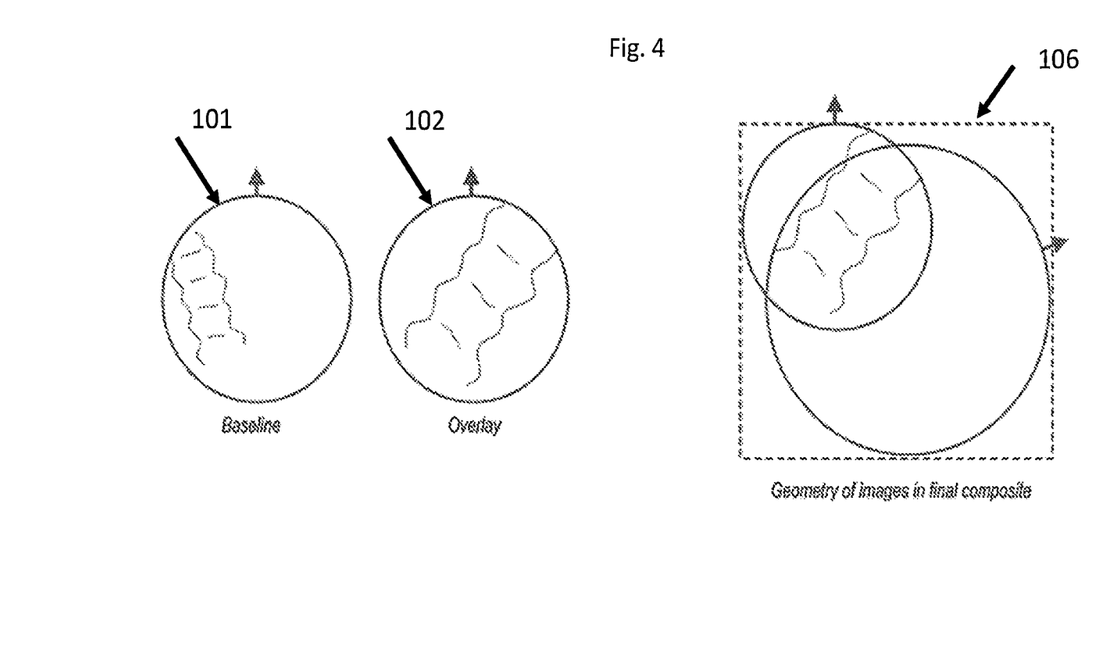
FIG. 4 shows an exemplary alignment scheme of the baseline and overlay images and spatial transformation to the baseline image.

In some embodiments, the baseline image is spatially transformed according to the estimated alignment to align with the overlay image or any reference coordinate system. Pixels of the baseline image can be linearly interpolated if needed. The spatial transformation can include one or more of translation, scale, and rotation. FIG. 4 shows an exemplary spatial transformation of the baseline image 101 to generate the composite image 106. FIGS. 2A and 2D show examples of the transformed baseline image 201 disclosed herein.

In some embodiments, the methods and systems can create a Boolean mask image for the transformed baseline 201 and overlay images 102 to flag which pixels are inside the "active area" in each, e.g., a circular area. Different versions of the mask can be created. For example, one mask can be extending exactly to the edge of the black border, the other mask can be stopping inward from the edge by a small distance. The second mask may serve as a conservative mask (with user-selectable margin distance) to avoid poorly-estimated image radius, and other quality problems at the edge.

Figure 6A:
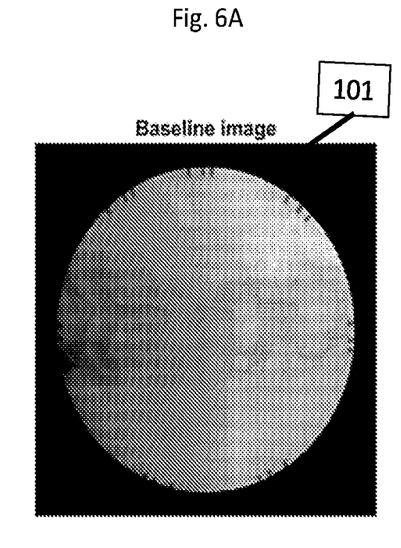
FIGS. 6A-6C show an exemplary baseline image (FIG. 6A), overlay image (FIG. 6B), and a scatterplot of pixel intensities after alignment (FIG. 6C)
Figure 6B:
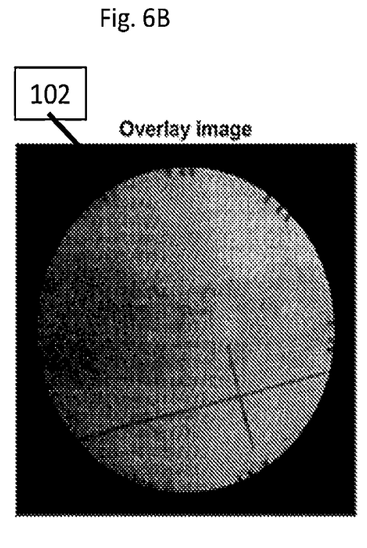
Figure 6C:
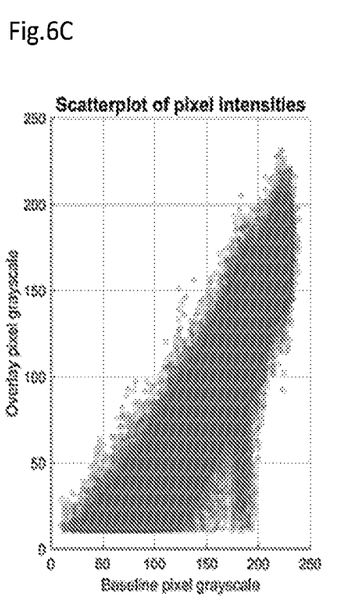

A step before generating the difference image 106 can be to equalize the brightness and/or contrast of the baseline 101, 201 and overlay image 102. Usually, the overlay image can be taken at a lower dose, hence cannot be assumed to have the same contrast setting as the baseline. For example, FIG. 6A-6B shows a baseline 101 and overlay 102 pair (left and middle panels), where the overlay is noticeably darker. When aligned, the grayscale values of corresponding pixels in the two images may fit well to a line (right panel in FIG. 8). Intensity and/or contrast difference of the baseline and overlay pixels can be modeled as a linear function, then the linear function can be used to rescale the overlay image to match the baseline image. In some embodiments, intensity and/or contrast difference of the baseline and overlay pixels can be modeled as a non-linear function. Such non-linear function can be used to rescale the overlay image to match the baseline image.

Assume the baseline 101 and overlay images 102 can differ by an arbitrary contrast and brightness difference, as a result of switching to low dose. This difference ca be modeled as a linear transformation:

$$\text{overlay image} = A * (\text{baseline image}) + B \quad (1)$$

For some unknown scale change A and offset B. Estimating their values can be a linear regression problem. Majority of pixel in both images may follow this pattern, for a fixed A and B, but not every pixel may fit the equation (1) perfectly. There can be some error from background noise, spatially-varying intensity changes, presence of metal, saturated regions (either all black or all white), etc. In some cases, the pixels of metal can't be masked out from the linear fit. In some embodiments, the systems and methods select contributing pixels to the fit base on the following criteria: 1) be inside overlap area of both baseline and overlay active image areas; 2) have a grayscale value sufficiently far from total black (e. g., 0) and total white (e.g., 255) for both images, to avoid using saturated pixels. The minimum away from these limits can be a user-settable parameter. This may or may not exclude metal pixels (near 0).The systems and methods herein can use different methods to improve the robustness of the estimate of the line fit. In some embodiments, the estimate of line fit used here can be outlier tolerant. In some embodiments, the estimate of line fit herein may include: a robust nonparametric initial line estimate to cull spatially large outliers, and 2) an iterative linear regression step to refine the estimate in the presence of small outliers. In some embodiments, the estimate of the line may use linear regression or non-linear regression.

For poor quality (especially low-dose) images, the estimate of line fit may be overwhelmed by outliers, both random and systematic. For example, if part of the overlay image is saturated, the scatter plot may contain a horizontal line that steals focus from the desired line. To estimate a line in the presence of a large amount of outliers, the systems and methods herein may pull out subsets of the pixels in the overlay image, estimate a line from that subset, then take the median across a large number if not all subsets (for both slope and intercept). Using the median may reduce the influence of outliers compared to taking an average. In this case, each subset may contain two points; two points can be selected at random from the dataset and form the line connecting them.

Figure 7:
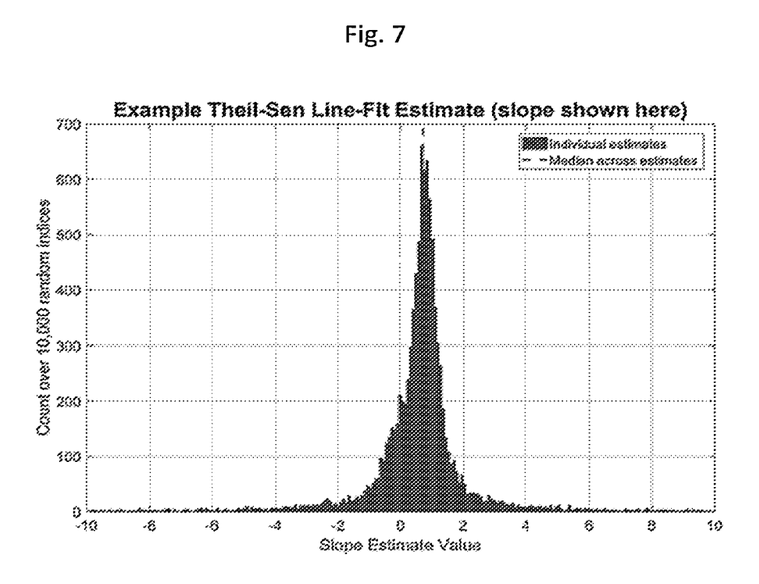
FIG. 7 shows an exemplary histogram for estimating a line fit that can be used to equalize brightness and contrast of the baseline and overlay images shown in FIGS. 6A-6B.
Figure 8:
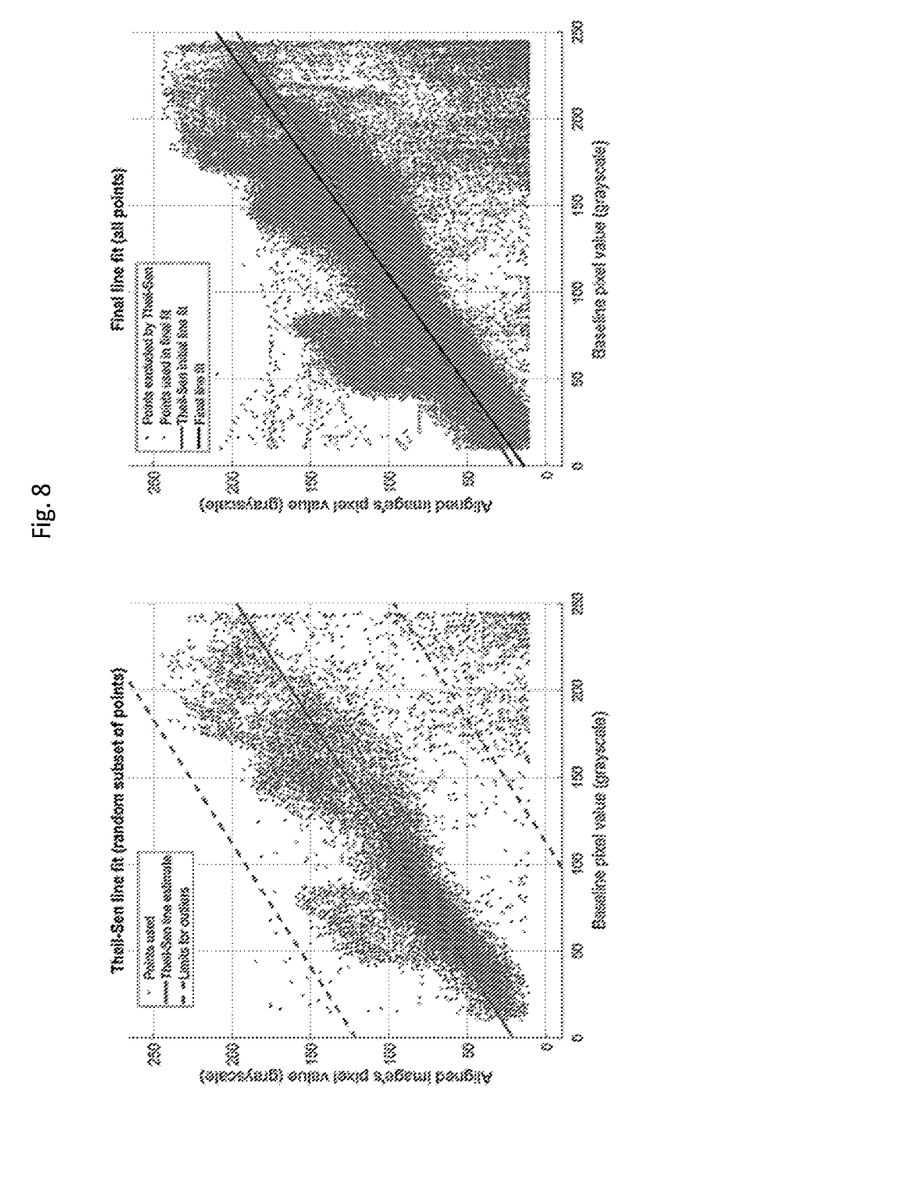
FIG. 8 shows an exemplary rough line estimate (left) and a final line fit (right) of the images in FIGS. 6A-6B.

As an exemplary embodiment, the initial or rough slope estimate can be the median of slopes, each slope of a line fit through randomly-paired points, the points can be non-repetitively selected. In this embodiment, the initial or rough intercept estimate can be median of intercepts, each intercept of a line fit through the randomly-paired points, the points can be non-repetitively selected The output of this initial or rough line estimation step can be used to discard points that are significantly far from the initial or rough line estimate, e.g., Theil-Sen line estimate, where the distance is a user-settable parameter. FIG. 7 shows an example initial estimate of line slope for one image pair. FIG. 8 shows, for this same image pair, an exemplary scatterplot of pixels in the overlap area for the two images, with the initial line estimate and the boundary lines at the Theil-Sen outlier thresholds (left). Outlies that are outside of the boundary lines are removed from consideration in subsequent line fitting step(s).

In some embodiments, points that survive the initial line estimate step are passed to a linear regression function to estimate the slope and intercept parameters. An iterative refinement of the estimates can performed to gradually culls more outliers from the best-fit line. An exemplary flow of iterative steps can be as follows: 1) applying linear regression using the remaining pixels. or the first iteration, the dataset of pixels includes points not discarded by the initial step; 2) discarding points beyond X standard deviations of the estimated line in the current iteration, where X can be set by a user, e.g., X can be set to 2; 3) repeating steps 1) and 2) until a stopping criterion is met.

The iterative loop can be halted if the slope and intercept estimates converge (e.g., changes in value less than about 1% from the previous iteration), if less than 30 points survive, or if a max of 100 iterations is reached. FIG. 8 shows an exemplary embodiment of the raw data, initial line estimate (left), and subsequently robust line fit (right) for an example image pair, wherein the horizontal axis is the baseline image grayscale, and the vertical axis is the aligned overlay image grayscale.

In some embodiments, criteria on line fit output can be used to determine whether to proceed to the next stage. For example, the criteria can include one or more of: 1) the goodness of fit (e.g., coefficient of determination, or $R^2$) the line estimation may exceed a user-settable threshold. Note this $R^2$ can be computed on the final surviving set of points after the iterative estimation, not on the entire set. The minimum $R^2$ can be manually set.

In some embodiments, lower and upper limits on both slope and intercept are manually added base on prior knowledge of the imaging modality and/or image capturing device. The limits can be determined empirically. Exemplary slope range can be [0.16, 3.0] and exemplary intercept can be in the range [−200, 200].

In some embodiments, noise estimate of the overlay image can be used to predict whether the blend may be visually unacceptable, and reject (fail) images over a predetermined threshold in noise. The threshold may or may not be fixed or constant. Using the overlay image's noise value for quality thresholding can be dependent on certain assumptions: 1) the baseline image is assumed high-dose and thus has negligible background noise compared to the overlay; 2) the amplitude of the contrast in the anatomy is assumed fixed from image to image; 3) the noise intensity across the image.

The background noise can be uncorrelated Gaussian white noise. In some cases, the noise may be modeled as Poisson and has some degree of spatial correlation. In some cases, the noise can be modeled using distributions that are not Gaussian. When the noise characteristics of typical C-arms are approximately constant from shot-to-shot, the correction to the noise estimate can be independent of image content or noise intensity.

Various method can be used for estimating Gaussian noise standard deviation in images e.g., Immerkaer's method (Immerkaer 1996, Tai 2008). It may apply the discrete Laplacian operator to the image and assumes the noise is proportional to the average intensity of the result. Given an image I(i, j) with row and column indices i,j and dimensions W, H, the estimate of noise can be:

$$\hat{\sigma}_{Immer} = \sqrt{\frac{\pi}{2}} \cdot \frac{1}{6(W-2)(H-2)} \sum_{i=1}^{W} \sum_{j=1}^{H} |(I * M)| \tag{2}$$

where * is the convolution operator, the hat (^) symbol denotes a statistical estimate, and M is the discrete Laplacian mask:

$$M = \begin{bmatrix} 1 & -2 & 1 \\ -2 & 4 & -2 \\ 1 & -2 & 1 \end{bmatrix}. \tag{3}$$

Pixels with grayscale values outside of a user-selectable range (e.g., [20, 235]) can be excluded from the estimation. The black border area beyond the circular field of view can also be excluded. The removal of these pixels can accounted for using:

$$\hat{\sigma}_{modified\ Immer} = \sqrt{\frac{\pi}{2}} \cdot \frac{1}{6(N_p - 4\sqrt{N_p})} \sum_{i=1,ij\in G}^{W} \sum_{j=1,ij\in G}^{H} |(I*M)| \quad (4)$$

where Np is the number of pixels remaining after culling and G is the set of pixels that survived the culling. The term $(N_p - 4\sqrt{N_p})$ is a modification adjusted to account for the number pixels removed, and the summations are now only done over pixels that survived. The final noise estimate can then rescaled to match how the overlay image can be rescaled:

$$\hat{\sigma}_{resc} = \frac{\hat{\sigma}_{modified\ Immer}}{A} \quad (5)$$

where again A is the estimated slope of the linear fit between baseline and overlay as modeled in Equation (1). This estimated standard deviation can be the threshold—any image with rescaled noise greater than a pre-determined fixed threshold is rejected.

In some embodiments, the systems and methods utilizes steps to ensure optimal or otherwise satisfactory equalization of image intensity and/or contrast of the baseline and overlay images. Such method steps may involve examination of a "Residual Image" that equals Baseline minus (overlay after equalization). If the fit is successful, residuals can approximately match the background noise in the image. The standard deviation of residuals can be compared to background noise to determine the match. The background noise in overlay image can be calculated using a high pass filter. When the residuals dramatically bigger than noise (e.g. 10×) may indicate unsatisfactory fit.

Such method steps may involve examination of "hotspots" in residuals—areas of image where the fit is poor (residuals too large). If objects of interest happen to fall in a poorly-fit area, the fit can be unsatisfactory. For this step, proportion of proportion of residuals in each local area with values greater than threshold in image may be used as an index of goodness of fit.

In some embodiments, residual-related measurements are not independent of each other, thus different local measurements can be combined into a single score.

Such method steps may involve examination of overall $R^2$ of the line fit.

Such method steps may involve examination of overall intensity of the overlay image to guard against too-dark images. In some cases, if the metal is faint in overlay, can be as faint in boosted composite image. If overlay image is a very dark image overall, the black pixels in metal might not be much darker than the background. To reject "too dark" overlay images, the systems and methods may count how many pixels are below a grayscale intensity cutoff (X), and stop the boosting if this is more than a predetermined percentage of the total pixels in image are too dark.

Rescaling

In some embodiments, given the estimated fit parameters, e.g., A and B in Equation (1), the overlay image can be rescaled:

$$\text{Rescaled overaly} = \frac{(\text{Original overlay} - B)}{A} \quad (6)$$

The baseline images 101 may be similarly rescaled to match the rescaled overlay images 202, if needed. A "difference image" can be calculated as the difference of the spatially-transformed baseline and rescaled overlay:

difference image=(Transformed baseline)−(Rescaled overlay) (7)

Figures 2E, 2F:
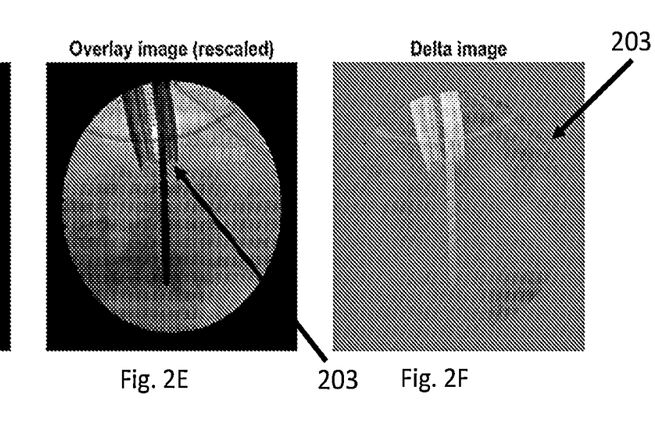

In some embodiments, the overlay image may be rescaled using parameters of a non-linear fit. FIGS. 2B and 2E show exemplary rescaled overlay images 202, and FIGS. 2C and 2F show exemplary difference images 203, each obtained using the transformed baseline images 201 and the rescaled overlay images 202. After obtaining the difference image, the systems and methods herein can advantageously avoid both image segmentation and a hard thresholding. Instead, a "soft thresholding" approach that is designed to be more forgiving of misclassification may be used herein. Instead of a simple Boolean separation of metal and not metal, each pixel can be assigned a degree of its likelihood of being metal, e.g., a range between 0 and 1 indicating how likely that pixel is to be metal. Then each final pixel in the composite can be a proportional mix of the baseline and rescaled overlay image. In some cases, the more likely a pixel is to be metal, the higher the proportion comes from the overlay image. A visible artifact at the metal's border may also be avoided, as pixels at the boundary may be a smooth blend from both images.

The systems and methods herein can build a "soft" mask from the difference image. The steps in the process of finding such a mask can include one or more steps disclosed herein.

In some embodiments, grayscale values in the difference image 203 that are characteristic of 1) background and 2) metal may be found. In some embodiments, the systems and methods include a step of finding the grayscale values. This can be done by generating a histogram of the difference image 203, e.g., in the overlap region. As an example, most background pixels can be around zero, and metal pixels can clustered at brighter non-zero values.

The mode of the histogram (the bin with the highest histogram value) can be at approximately the mean background level. The mode can be taken after smoothing the histogram, to reduce the chance of being fooled by a spurious noise peak in the history. As the background may be close to zero, the background mean is permitted to be within 10 standard deviations of the estimated noise level. This threshold can be determined empirically and can be changed.

Another step can be finding the grayscale value characteristic of metal. Unlike background, there is no knowledge a priori as to which value the metal grayscale value can center on. The grayscale for metal can depend on the density of the metal object and the relative contrast and/or brightness difference between the two images. Furthermore, many instruments can vary in thickness across their extent in the image. The metal objects might be of any size in the image, so very small items may contribute very little to the histogram's shape. The following schemes for finding a metal threshold grayscale value may not function optimally: 1) draw a threshold at a given number of noise standard deviations above the background mean level. This uses no information from actual metal pixels, and depends on the accuracy of the noise estimate previously described; 2) identify a second peak in the histogram to the right of the background peak. Metal may not be constant in color, so it is more likely to observe a broad tail to the right side of the histogram rather than a concentrated peak. Even if the metal is constant in color, the item might be too small for a peak to stand out in the histogram—it may simply be a shoulder on the background's peak; 3) identify a valley between background peak and metal peak in histogram. However, a valley may not exist (if the metal "peak" is so small that it is just a shoulder on the side of the background peak), or there may be multiple candidate valleys. Peak hunting (and its inverse, valley hunting) can be fragile in the presence of noise.

In some embodiments, at the best or otherwise optimal metal threshold, the Boolean image created using that threshold, e.g., metal=white, background=black, may look very similar to the raw difference image, where metal is bright and background is dark. If the threshold is varied, the candidate Boolean image can be compared to the difference image for similarity, then the threshold with a desired similarity, e.g., highest similarity, can be selected.

In some embodiments, the systems and methods herein utilize a procedure for finding such a threshold is as follows: 1) set an allowed range for a threshold. For example, the minimum can be the background gray mean level and the maximum can be 99% of the grayscale value. Such percentage can be set by the user. Putting the maximum value just below 100% may help avoid extreme outliers (e.g. one extremely bright pixel); 2) rescale the difference image. For example, the mean background can be set to −1, all pixels below this are clamped to −1, and the maximum value is set to +1; 3) vary the grayscale threshold in the allowed range. For any given threshold value, apply the threshold to the difference image to create a Boolean image, then cross-correlate this Boolean image with the rescaled difference image in step 2. This cross-correlation value can be the metric used to calculate similarity and decide on the best threshold. 4) Use a gradient descent algorithm to maximize the cross correlation in the threshold value. The search can start at a user's selected initial value, e.g., mean of the allowed threshold range.

In some embodiments, numerical optimization may be used in the systems and methods herein. For example, gradient descent can be used for the optimization. For gradient descent, the step size for each iteration can be computed using the Barzilai-Borwein method. Let t indicate the value of the gray level threshold, $t_n$ be the current estimate of the best metal threshold at iteration n, $C(t_n)$ be the cross-correlation of the Boolean image with the raw mask at threshold $t_n$, and $\nabla C(t_n)$ be the derivative of $C(t_n)$ with respect to threshold at the location $t_n$. Then the gradient descent equation for computing the next iteration's threshold estimate is:

$$t_{n+1} = t_n - \gamma_n \cdot \nabla C(t_n) \quad (8)$$

where the step size is determined by:

$$\gamma_n = \frac{(t_n - t_{n-1}) \cdot (\nabla C(t_n) - \nabla C(t_{n-1}))}{(\nabla C(t_n) - \nabla C(t_{n-1}))^2} \quad (9)$$

This method can permit the next step size to use information about the local slope, which may speed up convergence.

"Soft Threshold" for Identifying Metal

Based on the metal threshold, grayscale levels in the difference image can be determined as either corresponding to background where the baseline and overlay images are showing the same anatomy or corresponding to dark metal in the overlay image. Pixels can be classified as "anatomy" or "metal according to their grayscale value in the difference image. But this discrimination may not be very accurate. In some embodiments, a "soft threshold" rather than a hard cutoff is used to further classify the metal pixels. In some cases, pixels are given a weight, e.g., between 0 and 1, to signify how likely they come from metal, e.g., where 0=definitely anatomy, 1=definitely metal). Each pixel's weight can be calculated as a function of its grayscale value in the difference image, ramping up in a smooth sigmoid shape from the background mean level to the optimal metal threshold.

Various functions that can smoothly increase from 0 to 1 may be used as the weight function. For example, the sigmoid function can give the weight $\omega(x)$ as the function of the grayscale value x of a pixel in the form $$\omega(x) = \frac{1}{1 + Q \exp(-B \cdot x)} \quad (10)$$

Where x is the grayscale value of the pixel in the difference image, and Q and B are chosen to force the value of the weight at the background mean level and optimal metal threshold to be specific values. Let t1 be the mean grayscale value of the background, t2 be the optimal metal threshold disclosed herein. If the output weight is to equal w1 when x=t1 and to equal w2 when x=t2, then $$B = \frac{\ln\left[\left(\frac{1}{w_1 - 1}\right) / \left(\frac{1}{w_2 - 1}\right)\right]}{t_2 - t_1} \quad (11)$$

$$Q = \frac{\left(\frac{1}{w_1 - 1}\right)}{\exp(-B \cdot t_1)} \quad (12)$$

Figure 9:
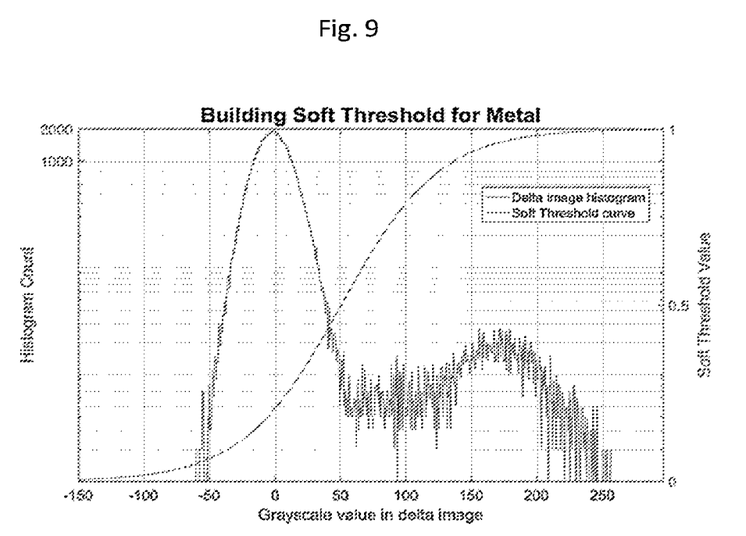
FIG. 9 shows an exemplary soft threshold curve for the images shown in FIGS. 2A-2C.

The values of w1 and w2 can be selected, e.g., w1=0.2 and w2=0.8. FIG. 9 shows an exemplary soft threshold sigmoid curve for the image pair in FIGS. 2A-2B. The weight curve can indicate how likely the pixel to be from overlay-image metal, ranging from 0 (not metal) to 1 (definitely metal). In the intermediate range, the weight is in the middle of its range.

Weight Mask

In some embodiments, the systems and methods includes one or more steps that use the soft weight values to construct a hybrid image. Instead of an "either/or" assembly of a hybrid image depending on whether each pixel is above or below some hard cutoff, each pixel can be a linear combination of corresponding pixels from both images, with the weight determined from Equation (10) governing the proportion coming from the overlay image. Thus pixels with a weight near zero (who are deemed from the dark background) may come mostly from the baseline image. In some embodiments, if neither image contains metal at a particular pixel, the pixel from the baseline can be used to preserve quality of the anatomical information therewithin. Pixels with weights near one, e.g., metal, are pulled mostly from the overlay image.

The use of this soft threshold may soften the impact of misclassified pixels and avoid some visible artifact at the boundary between metal and non-metal. At the boundary, pixels can be mixed roughly evenly from both images, so the transition can be relatively smooth. A pixel that is misclassified as metal can be taken from the overlay image, where it may have a similar value to the baseline image and be in the same region of anatomy.

Figure 3A:
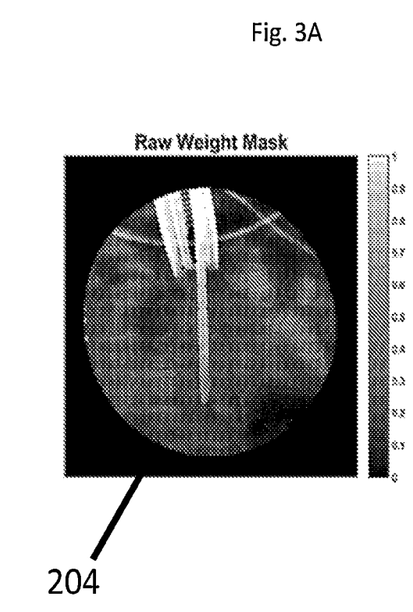
FIGS. 3A-3C show exemplary weight mask, smoothed weight mask, and final weighted mask that accounts for the region where overlay image extends past the edge of the baseline (white crescent at top) for the images shown in FIGS. 2C-2F.
Figure 3B:
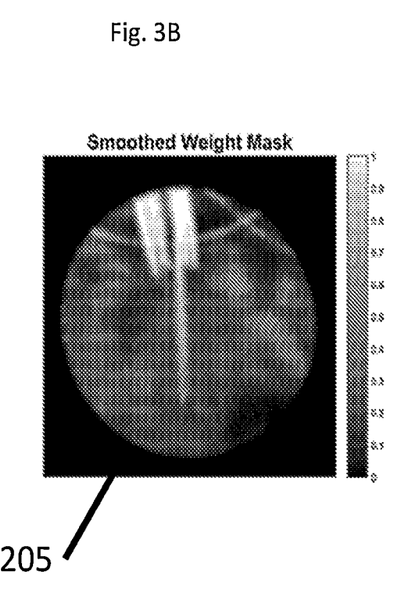
Figure 3C:
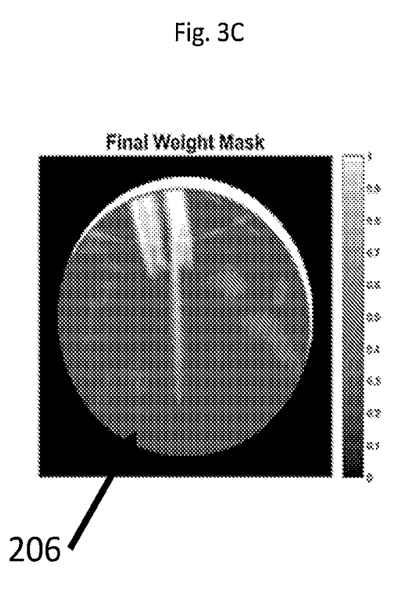

In some embodiments, a weight mask image, which has same size as final composite image can be generated, where each pixel can hold the weight derived from the soft threshold. FIGS. 3A-3C show an example weight mask 204, 205, 206 created for the images from FIGS. 2D-2E. The mask can be smoothed using various smoothing functions, for example using a Gaussian kernel of user-selectable width, then is set to either 0 or 1 as appropriate in the non-overlap regions (e.g. the white crescent at the top of the image in). If desired, the weight can be "rounded off" near the edge of the baseline image to smooth over any artifact at the edge of the baseline image.

Composite Image

In some embodiments, the final metal-boosted image is a composite image 106 of baseline 101 and overlay 102 with contributions in each pixel determined by the weight mask 204, the smoothed weight mask 205, or the final weight mask 206 as disclosed herein. The value of each pixel in the composite can be a linear combination of the baseline and overlay images, in their raw and metal-enhanced versions. A pixel in the output composite can be constructed from the corresponding pixels in each input image according to the linear combination:

$$\text{Raw pixel value} = \omega[(1-\varepsilon)\cdot RO + \varepsilon \cdot ROE] + (1-\omega)[(1-\varepsilon)\cdot BT + \varepsilon \cdot BTE] \quad (13)$$

where BT can be baseline image that has been transformed via output of alignment (Tx, Ty, Scale, Angle), RO can be overlay image, rescaled in intensity to match the baseline's brightness & contrast, BTE can be transformed baseline image that has been metal-enhanced using an enhancement filter herein, ROE can be the overlay image, metal enhanced, and $\omega$ can be for a given pixel, the value of the weight mask image, and $\varepsilon$ can be the input desired amount of metal enhancement filter (user input, in the range 0 to 1).

The raw grayscale value from Equation (13) can be rescaled in to a desired grayscale range, e.g., [0, 255]. Two exemplary processes for rescaling of the final grayscale range can be: 1) force usage of the dynamic range of the baseline mage. This assumes the baseline image can be acquired at good contrast/brightness settings. By rescaling the overlay image it is converted to the "units" of the baseline, the composite image is clamped to the range [0, 254]. The actual min/max range of the baseline and final range it is clamped to are user settable. The output composite will thus have the same brightness/contrast appearance as the baseline; 2) adjust the dynamic range proportional to the baseline amount. In this case, the output dynamic range was set to a combination of the baseline and original overlay image's dynamic ranges, proportional to the input value of the baseline amount. As the user varies the baseline amount from 100% baseline to 0% baseline, the output image's brightness/contrast will gradually change from matching baseline to matching overlay.

In some embodiments, the composite image can be resized to a desired side, e.g., to fit inside the input dimensions (width and height).

Edge Enhancement

Figure 5A:
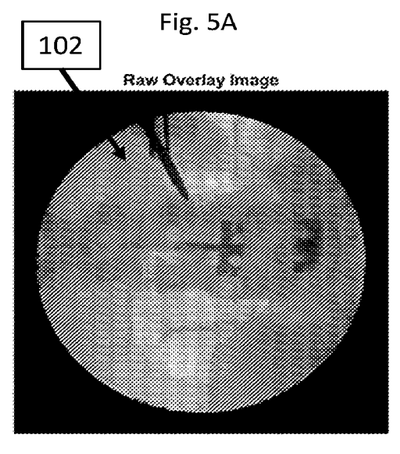
FIG. 5 shows an exemplary overlay image (left) and the enhanced image (right) by applying an enhancement filter disclosed herein.
Figure 5B:
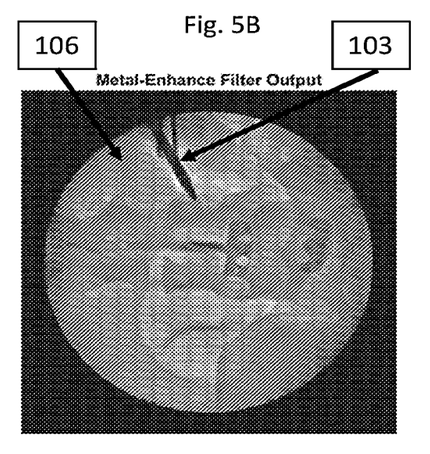

In some embodiments, the systems and methods herein may emphasize or enhance edges in the composite image. As an example, a metal-enhancement filter can be used for edge enhancement. The filtered result can be mixed in the enhanced version of each image into the final blend of the composite image. The strength of edge enhancement can be dialed up or down manually or automatically. In some embodiments, an edge-enhancement filter may be used to enhance the appearance of dark lines or edge in the images, which tends to preferentially darken metal and bone borders. The filter may function to smooth high-frequency noise and enhancing edges. Artificial objects (usually metal) and edges of bone are thus enhanced. The result gives the image an "embossed" look, smoothing out high-frequency noise and increasing the contrast of faint edges. An example of edge filtering and enhancement is shown in FIGS. 5A-5B.

Output Image Geometry

As shown in FIG. 4, in an exemplary embodiment, a single image can be returned containing a Venn-diagram shaped mosaic of baseline 101, 201 and overlay 102, 202 on a black background. The overlay image, optionally rescaled, can be "upright" (at the same orientation as the original shot) in the composite image 106, and the baseline is transformed according to an alignment transform. FIG. 4 shows an exemplary embodiment for a pair of baseline and overlay images that differ by a scaling and a rotation factor. The border of the output composite image 106 can be the smallest rectangle that circumscribes both images.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

What is claimed is:

1. A method for adjusting appearance of objects in medical images, the method comprising:
receiving, by a computer, a baseline image of a subject containing one or more objects therewithin, the baseline image taken with a baseline image quality and a baseline radiation dosage;
receiving, by the computer, an overlay image of the subject containing the one or more objects therewithin, the overlay image taken with an overlay image quality and an overlay radiation dosage;
transforming, the baseline image using a spatial transformation thereby generating a transformed baseline image, wherein the transformation comprises one or more of spatial scaling, translation, and rotation factors;
equalizing image intensity, image contrast, or both of the baseline image and the overlay image by estimating an image equalizing transformation between the baseline image and the overlay image;
rescaling, by the computer, the overlay image using the scaling factor and the offset thereby generating a rescaled overlay image;
generating, by the computer, a difference image of the transformed baseline image and the rescaled overlay image;
generating, by the computer, a smoothed weight mask, wherein each pixel of the smoothed weight mask is a weighting; and
generating, by the computer, a composite image of the baseline image and the overlay image with contribution of the baseline image and the overlay image determined by the smoothed weight mask wherein the smoothed weight mask includes using soft weight values to construct a hybrid image, wherein the hybrid image is based on whether each pixel is above or below a defined cutoff value, and each pixel is a linear combination of corresponding pixels from multiple images, with the smoothed weight mask determined from an equation governing the proportion from the overlay image.

2. The method of claim 1, wherein the overlay image quality is lower than the baseline image quality.

3. The method of claim 1, wherein a first signal to noise ratio of the overlay image is lower than a second signal to noise ratio of the baseline image.

4. The method of claim 1, wherein the image equalizing transformation is a linear transformation determined by a scaling factor and an offset.

5. The method of claim 1, wherein the difference image is obtained by subtracting the rescaled overlay image from the transformed baseline image.

6. The method of claim 1, wherein the weighting is determined by intensity of a corresponding pixel in the difference image, estimated intensity of background pixels in the difference image, and estimated intensity of one or more objects in the difference image, or a combination thereof.

7. A method for adjusting appearance of objects in medical images, the method comprising:
  receiving, by a computer, a baseline image of a subject containing one or more objects therewithin, the baseline image taken with a baseline image quality and a baseline radiation dosage;
  receiving, by the computer, an overlay image of the subject containing the one or more objects therewithin, the overlay image taken with an overlay image quality and an overlay radiation dosage;
  transforming, the baseline image using a spatial transformation thereby generating a transformed baseline image, wherein the transformation comprises one or more of spatial scaling, translation, and rotation factors;
  equalizing image intensity, image contrast, or both of the baseline image and the overlay image by estimating an image equalizing transformation between the baseline image and the overlay image;
  rescaling, by the computer, the overlay image using the scaling factor and the offset thereby generating a rescaled overlay image;
  generating, by the computer, a difference image of the transformed baseline image and the rescaled overlay image;
  generating, by the computer, a smoothed weight mask, wherein each pixel of the smoothed weight mask is a weighting; and
  generating, by the computer, a composite image of the baseline image and the overlay image with contribution of the baseline image and the overlay image determined by the smoothed weight mask,
  wherein the smoothed weight mask includes using soft weight values to construct a hybrid image, wherein the hybrid image is based on whether each pixel is above or below a defined cutoff value, and each pixel is a linear combination of corresponding pixels from multiple images, with the smoothed weight mask determined from an equation governing the proportion from the overlay image.

8. The method of claim 7, wherein the overlay image quality is lower than the baseline image quality.

9. The method of claim 7, wherein a first signal to noise ratio of the overlay image is lower than a second signal to noise ratio of the baseline image.

10. The method of claim 7, wherein the image equalizing transformation is a linear transformation determined by a scaling factor and an offset.

11. The method of claim 7, wherein the difference image is obtained by subtracting the rescaled overlay image from the transformed baseline image.

12. The method of claim 7, wherein the weighting is determined by intensity of a corresponding pixel in the difference image, estimated intensity of background pixels in the difference image, and estimated intensity of objects in the difference image, or a combination thereof.

* * * * *